| United States Patent [19] | [11] Patent Number: 4,988,693 |
| Detre et al. | [45] Date of Patent: Jan. 29, 1991 |

[54] FUNGICIDE COMPOSITIONS

[75] Inventors: Tamás Detre, Nagymaros; Lajos Rejtő, Budapest; József Sós, Budapest; András Szegő, Budapest; Ferenc Virányi, Budapest; Tibor Érsek, Budapest; Gyöngyvér Nagy née Hegyi, Budapest; László Hornok, Budapest; Attila Molnár, Pásztó; Erzsébet Schüszler, Budapest; Sándor Ángyán, Budapest; Katalin Mármarosi, née Kellner, Biatorbágy; Lyr Horst, Eberswalde; Dieter Zanke, Potsdam; Brita Lenner, Kleinmachnow; Marlies Strump, Potsdam; Gyula Oros, Budapest, all of Hungary

[73] Assignee: Chinoin Gyogyszer- Es Vegyeszeti Termekek Gyara, R. T., Budapest, Hungary

[21] Appl. No.: 290,108
[22] PCT Filed: Mar. 8, 1988
[86] PCT No.: PCT/HU88/00013
 § 371 Date: Dec. 5, 1988
 § 102(e) Date: Dec. 5, 1988
[87] PCT Pub. No.: WO88/06841
 PCT Pub. Date: Sep. 22, 1988

[30] Foreign Application Priority Data

Mar. 9, 1987 [HU] Hungary ............... 983/87

[51] Int. Cl.$^5$ ............. A01N 37/12; A01N 37/44; A01N 43/52; A01N 43/84
[52] U.S. Cl. ............... 514/231.2; 514/388; 514/539
[58] Field of Search ........... 514/539, 388, 231.2

[56] References Cited

PUBLICATIONS

The Pesticide Manual, 8th Ed., Worthing et al, (1987), pp. 49, 58, 59 and 827.

Primary Examiner—Allen J. Robinson
Attorney, Agent, or Firm—Herbert Dubno; Jonathan Myers

[57] ABSTRACT

The invention relates to synergistic combinations of known fungicide active ingredients and their application in plant protection.

4 Claims, No Drawings

1

FUNGICIDE COMPOSITIONS

FIELD OF INVENTION

The invention relates to synergistic combinations of known fungicidal active ingredients and their application in plant protection.

BACKGROUND OF THE INVENTION

N-alkyl-morpholines are applied as fungicides in plant protection (DE-PS Nos. 1164152 and 1198125 and DD No. 140112).

A disadvantage of the known agents is that they have only a narrow spectrum of activity, preferentially for mildew fungi (Erysiphales) in cereals. By their phytotoxic side effects they can be used only in a restricted field of application.

The various acylamide derivatives (DD Nos. 118 979 and 118 510, DE-PS Nos. 2 515 091, 1 448 810 and 2 903 612, GB-PS No. 1 603 730 and EP No. 26 873), on the other hand, possess a good efficacy against fungi from the group of Oomycetes, but they are inactive against other plant pathogenic fungi of economical importance.

Furthermore, it is known that benzimidazole- and dithiocarbamate fungicides are applied in plant protection to control fungal diseases (GB-PS Nos. 1 193 461, 1 190 614 and 1 000 137). A disadvantage of the benzimidazole fungicides results from the quick appearance of resistance in the target fungus population.

For simultaneous control of different species of fungi the use of a mixture of N-alkyl-morpholines with dithiocarbamates was recommended (DD No. 111 014).

It is also known that N-alkyl-morpholine derivatives in combination with methyl N-(2-methoxyacetyl)-N-(2,6-xylyl)-D,L-alaninate (HU-PS No. T/33363) are beneficially used against fungal disease.

DETAILED DESCRIPTION OF THE INVENTION

The object of the invention is, to enrich the prior art with fungicide compositions of better properties for the practical control of fungal diseases.

The invention is a fungicide composition containing in addition to the conventional carriers and auxiliaries, 5-95 by weight percent of an active ingredient mixture of the following components:

(A) one of the following acylamide derivatives:
methyl N-(2-methoxyacetyl)-N-(2,6-xylyl)-D,L-alaninate (Metalaxyl);
methyl N-(2-furoyl)-N-(2,6-xylyl)-D,L-alaninate (Furalaxyl);
methyl N-phenylacetyl-N-(2,6-xylyl)-D,L-alaninate (Benalaxyl);
±-alpha-2-chloro-N-(2,6-xylylacetamido)-gamma-butyrolactone (Ofurace);
(±)-alpha-[-N-(3-chlorophenyl)cyclopropanecarboxamido]-gamma-butyrolactone (Cyprofuram);
2-methoxy-N-(2-oxo-1,3-oxazolidin-3-yl)-2',6'-xylidide (Oxadixyl);
N-isoxazole-5-yl-N-(2,6-xylyl)-D,L-alanine-methylester (LAB 149202F);
N-(2,6-dimethyl-phenyl)-2-methoxy-N-(tetrahydro-2-oxo-furanyl)-acetamide (RE 26745); and (B) one of the following morpholine derivatives:
2,6-dimethyl-4-tridecylmorpholine (Tridemorph);
4-cyclododecyl-2,6-dimethylmorpholine (Dodemorph);

(±)-cis-4-[3-(4-tert-butylphenyl)-2-methylpropyl]-2,6-dimethylmorpholine (Fenpropimorph);
the mixture of N-alkyl($C_{12}$)-2,6-dimethylmorpholine and N-alkyl($C_{12}$)-2,5-dimethyl morpholine (Aldimorph);
together with
(C) one of the following fungicides
diethyl 4,4'(o-phenylene)bis(3-thioallophanate) (Thiophanata);
dimethyl 4,4'-o-phenylene)bis[3-thioallophanata] (Thiophanate-methyl);
methyl-benzimidazole-2-yl-carbamate (Carbendazim) or (BCM);
methyl-1-(butylcarbamoyl)benzimidazole-2-ylcarbamate (Benomyl);
2-(4-thiazolyl)-1H-benzimidazole (Thiabendazole); or (D) one of the following dithiocarbamate or disulphide derivatives:
zinc ethylenebis(dithiocarbamate) (polymeric) (Zineb);
manganese ethylenebis(dithiocarbamate) (polymeric) (Maneb);
manganese ethylenebis(dithiobarbamate) (polymeric) complex with zinc salt (Mancozeb);
zinc ammoniate ethylenebis(dithiocarbamate)-poly(ethylene thiuram disulphide) (Metiram);
polymeric zinc propylenebis(dithiocarbamate) (Propineb);
the mixture of Metiram [zinc ammoniate ethylenebis(dithiocarbamate)-polyethylenethiuram disulphide] and Propineb [polymeric zinc propylenebis(dithiocarbamate] in a ratio of 1:3 respectively (Polycarbazin)

In the compositions of the invention, the rate of the active ingredients A, B and C is 1:3-5:1-6, advantageously 1:4:4, the rate of the compounds A, B and D is 1:3-5:5-10 advantageously 1:4:10. The compositions according to the invention can be advantageously used to control diseases, which are caused by various species of fungi.

Surprisingly it was found that using the fungicide composition of the invention in the case of numerous species of fungi an increased activity may be observed, which is based on a synergistic rather than an additive action. This can be calculated e.g. according to the Colby's formula;

$$E = X + Y - \frac{X \cdot Y}{100},$$

wherein
X is the efficiency of the components A+B and
Y is the efficiency of the components C+D.

Another method is the HORSFALL model where the toxic effects of various treatments are compared at the same concentration level, i.e. each component of the fungicide mixture is tested at the total amount of the mixture applied, and the criterion of synergism was as follows:

$$LSD_{5\%}{}^{comb} < |X_i| = CT_i - MRV_{max},$$

wherein
$LSD_{5\%}{}^{comb}$=the lowest standard deviation at P=5% in the experiment,
$CT_i$=effect of the "i" variant of the treatment with the fungicidal mixture,
$MRV_{max}$=the maximum response value of the most toxic combination partner, if it was used alone at the total amount of the mixture concerned.

If $X_i$ positive, synergism, if $X_i$ negative, antagonism occurred.

In the SUN's model a Comparative Toxicity Index is used, which is calculated as follows:

$$Co.T.I. = \frac{1/ED_{50}^{mixt}}{\dfrac{a}{ED_{50}^Y} + \dfrac{b}{ED_{50}^Z}},$$

$ED_{50}$ = the efficiency of the known mixture Y,
$ED_{50}^B$ = the efficiency of the active ingredient Z
a and b indicate the current mass parts of the partners Y and Z in the combination.

An additional advantage of the composition of the present invention lies in a reduced risk of formation of resistance, that means in the reduced occurrence of fungal strains resistant to the above mentioned compounds under the selection pressure of the claimed fungicides. This is due to the different mode of action of the components, and to the absence of positive cross resistance among the components.

Due to the abovementioned reasons, the compositions according to the invention can be used for the reduction of heterogenous fungal populations, which at the conventional application of the individual components and/or their binary mixtures can not be controlled satisfactorily. Based on the systemic properties of some components, phytopathogenic fungi such as *Plasmopara halstedii* (Peronosporales, Ooomycetes), *Peronospora manshurica* (Peronosporales, Oomycetes), *Sclerospora graminicola* (Peronosporales, Oomycetes), *S.macrospora, Peronospora pisi* (Peronosporales Oomycetes), *Ustilago maydis* (Ustilaginales, Basidiomycetes), *Ustilago avenae* (Ustilaginales, Bsidiomycetes), *Fusarium oxysporum* (Deuteromycetes), Verticillium spp. (Deuteromycetes), *Rhizoctonia solani* (Polyporales, Basidiomycetes), *Stereum purpureum* (Basidiomycetes) etc. can be controlled effectively and newly developed parts of the plant can also be protected. With an optimal combination of the active ingredients according to the invention the following groups of phytopathogenic fungi can be controlled; powdery mildews, for example Erysiphe spp. (Erysiphales, Ascomycetes), Aspergillus spp. (Eurotiales, Ascomycetes), Penicillium spp. (Eurotiales, Ascomycetes), *Phoma betae* (Dothiales, Ascomycetes), *Ph. macdonaldii, Didymella applanta* (Dothiales, Ascomycetes), *Fusarium graminearum* (Hypocreales, Ascomycetes), *Nectria cinnabarina* (Hypocreales, Ascomycetes), *Venturia inaequalis* (Dothiales, Ascomycetes), *Khuskia oryzae* (Sphaeriales, Ascomycetes), *Colletotrichum atramantarium* (Sphaeriales, Ascomycetes), *Coll. dematium, Diaporthe phaseolorum* (Sphaeriales, Ascomycetes), *Phomopsis mali* (Sphaeriales, Ascomycetes), Ceratocystic ulmi (Sphaeriales, Ascomycetes), Botrytis spp. (Helotiales, Ascomycetes), *Sclerotinia sclerotiorum* (Helotiales, Ascomycetes), Ustilago spp. (Ustilaginales, Basidiomycetes) Verticillium sppl. *Rhizoctonia solani* (Polyporales, Basidiomycetes), *St. purpureum. Tr. versicolor, Sphaeropsis malorum*, Pythium spp. (Peronosporales, Oomycetes), Phytophthora spp. (Peronosporales, Oomycetes), *Albugo candida*, (Peronosporales, Oomycetes), *Bremia bectucae* (Peronosporales, Oomycetes), *Peronospora destructor* (Peronosporales, Oomycetes), *Plasmopara viticola* (Peronosporales, Oomycetes), *Pseudoperonospora cubensis* (Peronosporales, Oomycetes), Peronospora spp. (Peronosporales, Oomycetes), Alternaria spp. (Deuteromycetes), *Fusarium oxysporum* and other Fusarium spp. (Deuteromycetes), Verticillium spp. (Deuteromycetes). They are also useful against Gram-positive and Gram-negative bacteria (*Corynebacterium michiganese, C. nebraskense, C. flaccumfaciens* and *Xanthomonas malvacearem, X. phaseoli, X. translucens* pv. *oryzae*); and human related Bacillus, Staphylococcus and Streptomyces spp., too.

The compositions according to the invention can be formulated in a conventional way, e.g. to wettable powders, granulates or microcapsules, emulsion concentrates or flowables (WP, EC, FW, G, SD). For this purpose the active ingredients are dissolved in conventional liquid carriers, if desired, in the presence of surface active auxiliaries, dispergated respectively or admixed with solid carriers, or formulated according to other known processes.

The compositions of the invention are of 5 to 95 weight percent, advantageously 5 to 50 weight percent of the active ingredients. The compositions can be used in a conventional way, e.g. by spraying, dusting, submerging for dispersion or seed dressing.

The applied quantities depend on the aim of application and generally amount to 0.3 to 5 kg active ingredient/ha. The composition of the invention may be used for the treatment of sugar beet (*Beta vulgaris*), sunflower, soya, potato, tomato, corn, wheet, cucumber, vine, tobacco, broom-corn, millet, horse-bean (*Vicia faba*), cotton, citrus spp. apple, sugar-cane, avocado, mango (*Mungos mungo*), lettuce, onion, tulip, hyacinth, gladiolus (sword-lily), pea, bean, peanut, medic (Medicago), clover, batata (Xanthosoma spp.) plants susceptible to pathogenic fungal infections.

The composition according to the invention and their action are illustrated by the following examples.

EXAMPLE 1

In 508 g of water 21.2 g of Tensilin FN 80, 7.6 g of Tensiofix CG 21, 7.6 g of Tensiofix B 7425 are dissolved. To the solution under slow stirring 47.5 g of ethyleneglycol and under vigorous stirring 156 g of Carbendazim and 38 g of LAB 149202 are added. After homogenization the suspension will be transferred in an atritor of 1.5 liter content which contains siliquartizite pearls of 1 mm diameter. The atritor is operated for 30 minutes at 1440 RPM and later at 30 RPM. To the suspension the following solution is added: 156 g of Tridemorph, 4 g of Triton X-15, 31.2 g of Triton X-114. After stirring the suspension 16.8 g of paraffin oil and 1.8 g of Emulsogen M are added. After stirring the glass pearls (quartzite pearls) are separated by a screen. The floating capacity of the suspension concentrate amounts according to the CIPAC method to 95%.

EXAMPLE 2

In a powder homogenizer of 3 l capacity 200 g of Wessalon S are introduced. To 261 g of Tridemorph 6.6 g of Triton X-15, 52.8 g of Triton X-114 and 6.6 g of Triton X-45 are added. By slow stirring a homogeneous solution is prepared. This solution is added to Wesselon S while slow stirring. After further stirring 250 g of Carbendazim and 88 g of LAB 149202 are added. After 5 minutes of homogenization 50 g of Atlox 5320 and 75 g of Atlox 4862 are added and after further 5 minutes the mixture will be completed by the addition of 10 g of Aerosil. The powder mixture will be granulated in 2 parts in a laboratory granulator with water (to 500 g of the powder mixture 66 ml of water are added). The granulate formed is dried in a drying oven at 60° C. till constant weight. The particle size of the granulate amounts to 95% between 0.1 and 0.6 mm. The floating capacity of the product obtained amounts according to CIPAC to 84%.

EXAMPLE 3

In a homogenizer of 3 l content 150 g of Zeolex 414 are filled as a carrier. In a separate vessel 266 g of Tridemorph, 6.8 g of Triton X-15, 6.8 g of Triton X-45 and 54.2 g of Triton X-114 are mixed by stirring slowly. A homogeneous solution is obtained, which is transferred while uniform stirring in the homogenizer. After homogenizing 266 g of Carbendazim and 66.6 g of Benalaxyl are introduced. The mixture is homogenized, thereafter under continuous stirring 88.6 g of saccharose, 30 g of a wetting agent IS (Hoechst) and 65 g of sodium lignine-sulphonate are added.

The powder mixture is ground in an air jet mill to particles of 10 μm size. The floating capacity of the powder mixture obtained amounts according to CIPAC to 87%, the wetting time is 18 sec.

EXAMPLE 4

In an atritor of 1.5 l content 60.54 g of water and 6.55 g of ethylene glycol are mixed. To the solution 2.21 g of Tensiofix B 7425, 1.7 g of Tensilin FN 80, 12.5 g of Carbendazim and 3.1 g of Benalaxyl are added. The atritor is filled with siliquartizite glass pearls of 2 mm diameter and the mixing mechanism of the atritor is operated for 30 minutes with an RPS of 800. After this period the following solution is added to the suspension: 9.4 g of Tridemorph, 0.23 g of Triton X-15, 0.23 g of Triton X-45 and 1.84 g of Triton X-114 (preliminary homogenized).

After stirring, 1.35 g of paraffin oil and 0.15 g of Emulsogen M are added to the mixture. The siliquartzite glass pearls are filtered from the suspension. Applying a stirrer with a big shearing moment 0.2 g Tensiofix 821 are added to the solution.

The floating capacity of the suspension is according to CIPAC 97% (Particle size under 5 μm in 98%).

EXAMPLE 5

To 605.4 g of water 65 g of ethylene glycol, 22.2 g Tensiofix CG-21 and 17 g Tensilin FN-80 are added.

Applying a stirrer with a big shearing moment continuously 125 g of Carbendazim and 31 g of Metalaxyl are added to the solution. At a maximum RPS of the stirrer (12000/minute) the suspension is homogenized. The suspension is poured into a laboratory atritor of 1500 ml and the artitor is filled with ceramic pearls of 1 mm diameter. The stirrer of the atritor is operated with a maximum RPS (1440/minute) for 30 minutes. Thereafter into the atritor a solution of 94 g of Tridemorph, 2.3 g of Triton X-15, 2.3 g of Triton X-45 and 18.4 g of Triton X-114 is introduced and stirring is continued for another 5 minutes. From the suspension the glass pearls are removed by a screen. Applying a stirrer with a big shearing moment to the suspension a previously similarly suspended mixture consisting of 13.5 g of paraffin oil, 1.5 g of Emulsogen M and 2 g of Tensiofix 821 is added and is homogenized for 3 minutes. The floating capacity of the suspension obtained amounts according to CIPAC 92%. The average particle size lies under 5 μm (97%).

EXAMPLE 6

In a laboratory powder homogenizer of 3 l content 300 g of Wessalon are introduced. To 266 g of Tridemorph under slow stirring 4 g of Triton X-15, 4 g of Triton X-45 and 25 g of Triton X-114 are added. Under stirring the Tridemorph solution is slowly poured into the powder homogenizer. Thereafter while further stirring a mixture of 266 g of Carbendazim 66 g of Metalaxyl, 30 g of the wetting agent IS and 39 g of sodium lignine sulphate are added. After 2 minutes of post homogenization the powder mixture is ground in a laboratory air jet mill to particles under 10 μm particle size. The floating capacity of the powder mixture amounts according to CIPAC to 86%, the wetting time is 23 sec.

EXAMPLE 7

In a powder homogenizer of 3 l capacity 549.5 g of Wessalon S are introduced. To 131 g of Tridemorph 3.3 g of Triton X-15, 26.4 g of Triton X-114 and 3.3 g of Triton X-45 are added. By slow stirring a homogeneous solution is prepared. This solution is added to Wessalon S while slow stirring. After further stirring 175 g of Carbendazim and 44 g of LAB 149202 are added. After 5 minutes of homogenization 25 g of Atlox 5320 and 37.5 g of Atlox 4862 are added and after a further 5 minutes the mixture will be completed by the addition of 10 g of Aerosil. The powder mixture will be granulated in 2 parts in a laboratory granulator with water (to 500 g of the powder mixture 66 ml of water are added). The granulate formed is dried in a drying oven at 60° C. till constant weight. The particle size of the granulate amounts to 95% between 0.1 and 0.6 mm. The floating capacity of the product obtained amounts according to CIPAC to 84%.

EXAMPLE 8

In a homogenizer of 3 l content 575 g of Zeolex 414 are filled as a carrier. In a spearate vessel 133 g of Tridemorph, 314 g of Triton X-15, 3.4 g of Triton X-45 and 27.1 g of Triton X-114 are mixed by stirring slowly. A homogeneous solution is obtained, which is transferred under uniform stirring in the homogenizer. After homogenizing 133 g of Carbendazim and 33.3 g of Benalaxyl are introduced. The mixture is homogenized, thereafter under continuous stirring 44.3 g of saccharose, 15 g of a wetting agent IS (Hoechst) and 32.5 g of sodium lignine-sulphonate are added. Later the mixture is stirred for a further 3 minutes.

The powder mixture is ground in an air jet mill to particles of 10 μm size. The floating capacity of the powder mixture obtained amounts according to CIPAC to 87%, the wetting time is 18 sec.

EXAMPLE 9

In a laboratory powder homogenizer of 3 l content 648 g of Wessalon are introduced. To 133 g of Tridemorph under slow stirring 2 g of Triton X-15, 2 g of Triton X-45 and 12.5 g of Triton X-114 are added. Under stirring the Tridemorph-solution is slowly poured into the powder homogenizer. Thereafter while further stirring a mixture of 133 g of Carbendazim, and 33 g of Metalaxyl, 15 g of the wetting agent IS and 19.5 g of sodium lignine sulphonate are added. After 2 minutes of post homogenization the powder mixture is ground in a laboratory air jet mill to particles under 10 μm size. The floating capacity of the powder mixture amounts according to CIPAC to 86%, the wetting time is 23 sec.

Auxiliaries and filling materials used

(a) Surface-active materials (wetting agents and emulsifying agents)

Tensilin FN 80 (Kutrilin): alkyl-aryl-polyglycolether;
Triton X-15, X-45 and X-114 (Rohm and Haas): octyl-phenolpolyglycolether;
Tensiofix CG 21, B 7425 (Tensia): alkyl-aralkyl-sulphonate and phosphate, esters and non-ionic surface-active material mixtures respectively;
Emulsogen M (Hoechst): fatty alcohol-polyglycolether;
Atlox 5320 (Atlas ICI): non-ionic surface-active material;
wetting agent IS (Hoechst): Dialkyl-sulpho-succinate.

(b) Dispersing agents

Sodium-lignine-sulphonate;
Atlox 4862: Alkyl-aryl-sulphonate-formaldehyde-condensate.

(c) Anti-freezing agents

Ethylene glycol

(d) Filling and carrier materials

Wessalon S (Degussa): synthetic silicic acid;
Aerosil 300 (Degussa): silicic acid with great specific surface;
Saccharose;
Zeolex 414 (Zeofin): sodium-aluminium-silicate;
Paraffin oil.

(e) Sedimentation inhibitor

Tensiofix 821 (Tenzia): synthetic polysaccharide.

EXAMPLE 10

Efficiency against downy mildew of sunflower

Sunflower germlings with the root initials, 1–5 mm in length, were inoculated with zoospore suspension ($2.5 \times 10^5$ spore/ml) of the downy mildew fungus (*Plasmopara halstedii* (Farl.) Berlese et de Toni, Peronosporales, Oomycetes). Twenty four hours after inoculation the germlings were immersed into the aqueous solutions (emulsions) suspensions of the chemicals to be tested for 18 hrs. The germlings were then planted into sterile soil and grown in greenhouse until the evaluation of the effectivity of treatments. All measures not descripted in detail here, and the assessments were made as described by OROS and VIRAÁNYI (1987): Ann. appl. Biol. 110:53–63.

The efficiency of treatments was characterized by $ED_{50}$ (mg/l) value and the significance of synergistic effect was tested according to SUN (1950).

TABLE 1

Eradicant Effect of Benomyl, Tridemorph, LAB 149202F and of their mixtures against downy mildew of sunflower

| Active agent* combination, resp. | mass proportion of the active agents | $ED_{50}$ | Co.T.1 |
|---|---|---|---|
| 1. LAB 149202F | — | 19.08 | |
| 2. Tridemorph | — | 500 | |
| 3. Benomyl | — | 500 | |
| 4. 2 + 3 | 1:1 | 500 | |
| 5. 1 + 2 | 1:4 | 16.86 | |

TABLE 1-continued

Eradicant Effect of Benomyl, Tridemorph, LAB 149202F and of their mixtures against downy mildew of sunflower

| Active agent* combination, resp. | mass proportion of the active agents | $ED_{50}$ | Co.T.1 |
|---|---|---|---|
| 6. 1 + 2 + 3 | 1:4:4 | 6.55 | 1.70 |

*The active agents and their mixtures, respectively, were applied in a suitable mass proportion in the form of wettable powder (WP) of the following composition: 40% of the active agent, or mixtures thereof respectively; Emulsogen I-40, TWEEN 20, TWEEN 80, TWEEN 40, silicagel, Hyflosupercell, dextran, Polyethylene glycol 20 000 and cyclohexane, 4.0; 0.5; 0.5; 1.0; 10.0; 10.0; 22.0; 8.0; and 4.0 percent respectively.

EXAMPLE 11

Seed dressing against damping off fungi (Pythium, Fusarium in peas)

Seeds of the peas (*Pisum sativum* cv Gloriosa) were surface sterilized with 0.1% sublimate prior to dressing and treated thereafter with active agents formulated as 25 WP. To improve the adhesion at the dressing process, a TWEEN 80 solution was added. The dressed seeds were sown into an infested soil. 14 days after emergence both qualitative and quantitative evaluation of fungicidal efficacy were carried out.

The efficiency was calculated as follows:

$$\text{Efficiency \%} = 100 - \frac{A \times 100}{B}$$

A = Infection rate (%) of the treated plants,
B = Infection rate (%) of the control plants.

TABLE 2

Seed dressing against fungi causing damping off

| Active agent | Concentration mg/L a.i. | | Efficiency % |
|---|---|---|---|
| 1. Carbendazim | 2.0 | | 9 |
| 2. Metalaxyl + | 0.25 | } 1.25 | 85 |
| Aldimorph | 1.0 | | |
| 3. Metalaxyl + | 0.125 | } 1.25 | 92 |
| Aldimorph + | 0.5 | | |
| Carbenazim | 0.5 | | |

TABLE 3

Seed dressing against fungi causing damping off

| Active agent | Concentration mg/L a.i. | | Efficiency % |
|---|---|---|---|
| 1. vPropineb | 1.50 | | 0 |
| 2. Metalaxyl + | 0.25 | } 1.25 | 63 |
| Tridemorph | 1.0 | | |
| 3. Meatalaxyl + | 0.125 | } 1.325 | 91 |
| Tridemorph + | 0.5 | | |
| Propineb | 0.7 | | |

TABLE 4

Seed dressing against fungi causing damping off

| Active agent | Concentration mg/L a.i. | | Efficiency % |
|---|---|---|---|
| 1. Benomyl | 2.50 | | 28 |
| 2. LAB 149202F + | 0.5 | } 2.5 | 67 |
| Aldimorph | 2.0 | | |
| 3. LAB 149202F + | 0.5 | } 2.5 | 82 |
| Aldimorph | 1.0 | | |
| Benomyl | 1.0 | | |

The used 25 WP had the following composition 25 weight % active ingredient or ingredients, respectively;
5 weight % Ca-lignin-sulphonate
5 weight % Tween 80
17 weight % Silicic acid
45 weight % kaolin

EXAMPLE 12

Protective effect against *Phytophthora infestans* on tomatoes

Solanum lycopersicum—plants, cv. "Tamina" at four-leaf stage were drop-wet sprayed with the combinations in 25 WP form. The inoculation of the plants with a zoo-spore-suspension was carried out after the fungicide was dried up. After the inoculation the plants were kept for one day in a humid chamber at 16° C. to 18° C. and for five further days in the greenhouse at 20° C. Thereafter the typical leaf-lesions appeared and their extension was a measure for the intensity of infection.

TABLE 5

Protective effect against *Phytophthora infestans* on tomatoes

| Active agent | Concentration mg/L. a.i. | | Efficiency % |
|---|---|---|---|
| 1. Metalaxyl | 6 | } 30 | 61 |
| Aldimorph | 24 | | |
| 2. Zineb | 30 | | 18 |
| 3. Metalaxyl | 2 | } 30 | 84 |
| Aldimorph | 8 | | |
| Zineb | 20 | | |

TABLE 6

Protective effect against *Phytophthora infestans* on tomatoes

| Active agent | Concentration mg/L a.i. | | Efficiency % |
|---|---|---|---|
| 1. Propineb | 30 | | 27 |
| 2. Metalaxyl + | 6.0 | } 30 | 62 |
| Tridemorph | 24 | | |
| 3. Metalaxyl + | 2.0 | } 30 | 88 |
| Tridemorph + | 8.0 | | |
| Propineb | 20.0 | | |

TABLE 7

Protective effect against *Phytophthora infestans* on tomatoes

| Active agent | Concentration mg/L a.i. | | Efficiency % |
|---|---|---|---|
| 1. Maneb | 10 | | 40 |
| 2. Mancozeb | 10 | | 25 |
| 3. Oxadixyl + | 2 | } 10 | 47 |
| Tridemorph | 8 | | |
| 4. Oxadixyl + | 2 | } 10 | 45 |
| Mancozeb | 8 | | |
| 5. Oxadixyl + | 2 | } 10 | 65 |
| Maneb | 8 | | |
| 6. Oxadixyl + | 1 | } 9 | 78 |
| Tridemorph + | 4 | | |
| Maneb | 4 | | |
| 7. Oxadixyl + | 1 | } 9 | 65 |
| Tridemorph + | 4 | | |
| Mancozeb | 4 | | |

TABLE 8

Protective effect against *Phytophthora infestans* on tomatoes

| Active agent | Concentration mg/L | | Efficiency % |
|---|---|---|---|
| 1. Metiram | 5.0 | | 20 |
| 2. LAB 149202F + | 1.0 | } 5.0 | 54 |
| Tridemorph | 4.0 | | |
| 3. LAB 149202F + | 0.8 | } 5.8 | 28 |
| Metiram | 5.0 | | |
| 4. LAB 149292F + | 0.5 | } 5.5 | 68 |
| Tridemorph + | 2.0 | | |
| Metiram | 3.0 | | |

EXAMPLE 13

Effect on the growth of *Phytophthora parasitica*

The acetonic solution of the fungicides to be tested was in a suitable amount admixed to the agar media and 4 hours after pouring out the plates the Petri dishes were inoculated with 3-3 mycelium cuts; after an inoculation period of 72 hours the diameter of the cultures was measured. The growth inhibition was expressed—referred to the untreated control—according to the following equation:

$$100 - \left(100 \times \frac{X_{ij} - 7}{X_{ikontr.} - 7}\right) = \text{inhibition in \%},$$

wherein
$X_{ij}$ = population diameter measured on j-compounds (or combination thereof) containing a medium plate of the given species (i)
$X_{ikontr.}$ = population diameter measured on xenobiotica not containing medium plate of the given species i.

The data were analyzed by means of variance analysis and the results are summarized in Table 9.

TABLE 9

Effect of combinations of Tridemorph + Carbendazim + an acylamide derivative on the growth (colony diameters) of *Phytophthora parasitica* f.sp. *nicotianae* v ar tomato

| Active agent or combination | Concentration mg/L | | Inhibition % |
|---|---|---|---|
| 1. Metalaxyl | 2.6 | | 50 |
| 2. Tridemorph + | 1.0 | } 2.25 | 81.6 |
| Carbendazim + | 1.0 | | |
| RE 26745 | 0.25 | | |
| 3. Tridemorph | 1.0 | } 2.25 | 73.6 |
| + Carbendazim | 1.0 | | |
| + Ofurace | 0.25 | | |

EXAMPLE 14

Control of a mixed mildew infection on cucumber leaves

Both powdery and downy mildew pathogens when associated in a leaf disease complex on cucumber can severely damage the leaf surface causing a serious yield loss.

Series of leaf treatments were carried out when first symptoms occurred caused by powdery mildews (*Sphaerotheca fulginea* and *Erysiphe cichoracearum*, Erysiphales, Ascomycetes) and Downy mildew (*Pseudoperonospora cubensis*, Peronosporales, Oomycetes).

The disease development was checked after days from the treatment by counting the number of visible pustules on the leaves. The inhibition of disease rate was calculated and expressed in percent of the untreated control.

Results.

TABLE 10

| Active agents or combinations | ratio | Concentration Mg/L | Inhibition of disease rate (%) |
|---|---|---|---|
| 1. Benalaxyl | | 10 | 32 |
| 2. Tridemorph | | 10 | 55 |
| 3. Benomyl | | 10 | 26 |
| 4. 1 + 2 | (9:11) | 10 | 61 |
| 5. 1 + 3 | (9:10) | 10 | 21 |
| 6. 2 + 3 | (11:10) | 10 | 16 |
| 7. 1 + 2 + 3 | (9:10:11) | 10 | 72 |

EXAMPLE 15

Seed-dressing experiments with maize

The infection rate of maize seed lot by Fusarium species used for laboratory purposes amounted to 29.5%, but total contamination has reached 100% so it was unsuitable for sowing.

After the treatment the infection rate of 4×100 seed pieces was evaluated following an incubation on Papavizas-medium. The effect of combination (CHBA 6–11) was compared with the standard mixture Kolfugo Extra (20% Carbendazim)+Quinolate V-4-X (2.0 l/t+1.0 kg/t, respectively) commonly used in Hungary. The results are presented in Table 11.

TABLE 11

| Treatment | Dose g/kg | Agent mg/100 g seed | Infection rate of seed % |
|---|---|---|---|
| CHBA 6 | 2.0 | 312 + 312 + 76 | 0.25 |
| CHBA 7 | 2.0 | 262 + 350 + 88 | 0.75 |
| CHBA 8 | 2.3 | 306 + 306 + 76 | 0.00 |
| CHBA 9 | 2.8 | 263 + 350 + 87 | 0.25 |
| CHBA 10 | 2.3 | 306 + 306 + 76 | 0.50 |
| CHBA 11 | 2.8 | 263 + 350 + 87 | 1.0 |
| Kolfugo Extra + | 2.0 | 400 | |
| Quinolate V-4-X | 1.0 | 500 + 150 | 1.0 |
| Surface sterilized | — | — | 29,5 |
| Control | — | — | 100,0 |

TABLE 12

| Preparation | Active agent | rate of active act. agent formulation | | |
|---|---|---|---|---|
| | | agent | content g/1000 g | act. agent content |
| CHBA 6 | Tridemorph + BCM + LAB 149202 | 4:4:1 | 156 + 156 + 38 | 350 |
| CHBA 7 | —"— | 3:4:1 | 131 + 175 + 44 | 353 |
| CHBA 8 | —"— + Benalaxyl | 4:4:1 | 133 + 133 + 33 | 300 |
| CHBA 9 | —"— —"— | 3:4:1 | 94 + 125 + 31 | 250 |
| CHBA 10 | —"— + Metalaxyl | 4:4:1 | 133 + 133 + 33 | 300 |
| CHBA 11 | —"— —"— | 3:4:1 | 94 + 125 + 31 | 250 |

Apron 35 SP Metalaxyl
Kolfugo 25 FW BCM
Kolfugo extra BCM
Quinolate V-4-X Carboxin + Cu-oxyquinolate

EXAMPLE 16

Seed-dressing experiments with soyabean (Acternaria, Fusarium, Aspergillus)

The efficiency of the individual treatments was evaluated first in the laboratory by determining the composition of pathogens (the contaimination rate of 2×100 seeds of soyabean). In a field experiment, the yield of soyabean treated with different fungicides was measured, and expressed in kg/plot (2 m$^2$).

The results obtained are contained in Table 13.

TABLE 13

| Fungicide | Dose of formulation g/kg seed | Dose of active ingredient mg/kg seed | No. of seeds infected | kg/2 m$^2$ (mean of 4 replicates) | K 90 |
|---|---|---|---|---|---|
| CHBA 6 (TKL) | 2.0 | 312 + 312 + 76 | 5.5 | 2.15 | 108.6 |
| CHBA 7 (TKL) | 2.0 | 262 + 350 + 88 | 1.5 | 2.18 | 110.1 |
| CHBA 8 (TKB) | 2.3 | 306 + 306 + 76 | 2.5 | 2.30 | 116.2 |
| CHBA 9 (TKB) | 2.8 | 263 + 350 + 87 | 1.0 | 2.45 | 123.8 |
| CHBA 10 (TKM) | 2.3 | 306 + 306 + 76 | 1.0 | 2.05 | 103.5 |
| CHBA 11 (TKM) | 2.8 | 263 + 350 + 87 | 3.5 | 2.18 | 110.1 |
| Apron 35 SD | 2.0 | 700 | 16 | 2.03 | 102.5 |
| Kolfugo 25 FW | 2.8 | 700 | 11 | 2.07 | 104.5 |
| Control | — | — | 76.5 | 1.98 | 100.0 |

EXAMPLE 17

Possibility of control population of pathogenic fungi associated with the root rot complex of seedlings Plant at seeding stage are endangered by a number of soil- and seed-borne seedling- and foot diseases caused by fungi of various taxonomic position (usually named pathogene "associated with the root rot complex" of plants—of G. DIXON (1981): Vegetable Crop Diseases, The Macmillan Press Ltd, London).

It is possible to eliminate certain pathogenic species with an efficient fungicide preparate. However, the species non-sensitive to a given compound can build up in an explosive way. The use of broad-spectral fungicides may circumvent this problem. Such compounds, however, are often harmful pollutants of the environment. The accumulation of toxic materials (e.g. mercury, tin, aluminum or carcinogenic metabolite, such as ETU) can not be exluded and one must renounce their use. Against the highly efficient and selective fungicide preparations that are harmless to nature and mankind (e.g. Carbendazim, Metalaxyl), the target organisms (plant parasites) become quickly resistant. The resistance is due to genetic reasons. In the population of the pathogens there appear individuals that carry genes responsible for the reduction of fungicide sensitivity.

Individuals carrying such genes that had been treated with the given fungicide will increase in number dramatically, moreover, in the soil fungi of various taxonomic position are associated with the root rot complex that makes a necessity to use a broad-spectrum fungicide. The use of especially selected and optimized mixtures is necessary due to the requirement of treatment as highly selective as possible and at the same time combating the formation of established resistant populations to the given fungicides. In Table 14 a model experiment is shown, which proves that in the case of a fungal population consisting of individuals of different fungicide sensitivity and associated with root rot complex, by the appropriate combination of synergistically interacting fungicides a successful control can be achieved. Beside the fact, that the pathogens associated with root rot complex can be controlled with certainty, a synergistic fungicide combination will reduce costs and decrease pesticide pressure to nature simply due to its increased efficacy to the target organisms.

Furthermore there occurs an economic synergism too, by the reduced amount of chemicals applied for having the same effect, by the reduced costs of application, and the by insurance increased of yield due to decreasing the probability of resistance.

Performance of experiments

By means of somatic hybridization (Molnar et. al., (1985): Exp. Mycol. 9:326 -333.), and by means of mass selection of spontaneous mutants (Oros (1987): Tag.-Ber. Akad. LdW. DDR., Berlin 253, S 177–183), respectively, *Fusarium oxysporum* and *Phytophthora parasitica* strains/clones of extremely different fungicide sensitivity were prepared for the experiments. The efficacy of the fungicides was determined in conventional agar plates by measuring the radial mycelium growth after 48 hours.

Fungicide effect was characterized by the % of inhibition of radial growth of colonies.

As the survival of the population in the presence of a harmful factor is always determined by the most resistant part of this population, the Most Potent Treatment (MPT) was used for comparing efficacies in the experiment.

TABLE 14

Control of mixed populations consisting of *Fusarium oxysporum* and *Phytophthora parasitica* individuals of different fungicide sensitivity in the case of their simultaneous occurence on tomatoes.

| Active agents, combinations, resp. ratio | | Inhibition of fungal species | | (ED$_{50}$ mg/L) T$_i$/T$_{MPT}$[c] |
|---|---|---|---|---|
| | | F. oxysproum[a] | P. parasitice[b] var. nicotianae | |
| Carbendazim | | 42.7 | 125 | 12.5 |
| Tridemorph | | 86.6 | 518 | 51.8 |
| Metalaxyl | | 500 | 4.2 | 50 |
| 1 + 2 | (1:1) | 8.1 | 105 | 10.5 |
| 1 + 3 | (4:1) | 57.2 | 16.9 | 5.7 |
| 2 + 3 | (4:1) | 117 | 9.05 | 11.7 |
| 1 + 2 + 3 | (4:4:1) | 8.9 | 10.07 | 1.0 |

[a]A population consisting of resistant and sensitive strains to benomyl. Ratio 1:1
[b]A population consisting of resistant and sensitive strains to metalaxyl. Ratio 1:1
[c]T$_i$/T$_{MPT}$ = the factor, which shows how manyfold the concentration of the preparate should be increased to have the same effect as it was obtained at the application of the most potent one (No. 7).
T$_i$ = ED$_{50}$ value (mg/L) of the "i" treatment, and
T$_{MPT}$ = the ED$_{50}$ value (mg/L) of the most potent treatment (MPT).

What we claim is:

1. A synergistic fungicidal composition containing as active ingredients a synergistically effective mixture of:
   (A) methyl-N-phenylacetyl-N-(2,6-xylyl)-D,L-alaninate;
   (B) 2,6-dimethyl-4-tridecylmorpholine; and
   (C) one of the following fungicides:
   methyl-benzimidazole-2-yl-carbamate; or
   methyl-1-(butylcarbamoyl)benzimidazole-2-yl-carbamate;
   wherein the weight ratio of the Compound (A), Compound (B) and Compound (C) is 1:3 to 5:1 to 6.

2. A synergistic fungicidal composition containing as active ingredients a synergistically effective mixture of:
   (A) methyl-N-phenylacetyl-N-(2,6-xylyl)-D,L-alaninate;
   (B) 2,6-dimethyl-4-tridecylmorpholine; and
   (C) methyl-1-(butylcarbamoyl)benzimidazole-2-yl-carbamate;
   wherein the weight ratio of the Compound (A), Compound (B) and Compound (C) is 9:10:11.

3. A synergistic fungicidal composition containing as active ingredients a synergistically effective mixture of:
   (A) methyl-N-phenylacetyl-N-(2,6-xylyl)-D,L-alaninate;
   (B) 2,6-dimethyl-4-tridecyl-morpholine; and
   (C) one of the following fungicides:
   methyl-benzimidazole-2-yl-carbamate, or
   methyl-1-(butylcarbamoyl)benzimidazole-2-yl-carbamate;
   wherein the weight ratio of the Compound (A), Compound (B), and Compound (C) is about 1:4:4.

4. A synergistic fungicidal composition containing as active ingredients a synergistically effective mixture of:
   (A) methyl-N-phenylacetyl-N-(2,6-xylyl)-D,L-alaninate;
   (B) 2,6-dimethyl-4-tridecyl-morpholine; and
   (C) methyl-1-(butylcarbamoyl)benzimidazole-2-yl-carbamate;
   wherein the weight ratio of the Compound (A), Compound (B), and Compound (C) is about 1:4:4 or about 9:10:11.

* * * * *